United States Patent [19]

Parker

[11] Patent Number: 5,405,512
[45] Date of Patent: Apr. 11, 1995

[54] GAS SENSOR AND METHOD

[76] Inventor: Fred Parker, Pheasant Run, Gwinedd Valley, Pa. 19437

[21] Appl. No.: 264,266

[22] Filed: Jun. 23, 1994

[51] Int. Cl.$^6$ .................. G01N 27/26; H01H 31/02; G08B 21/00
[52] U.S. Cl. .................. 204/153.1; 204/401; 204/406; 204/431; 204/432; 204/412; 324/555; 324/693; 324/713; 324/718; 340/635
[58] Field of Search ............... 204/401, 415, 406, 431; 204/432, 412, 153.1; 324/555, 718, 693, 713; 340/635

[56] References Cited

U.S. PATENT DOCUMENTS

| | | | |
|---|---|---|---|
| 3,849,725 | 11/1974 | Mori | 324/713 |
| 4,260,985 | 4/1981 | Hayden | 340/635 |
| 4,845,435 | 7/1989 | Bohan, Jr. | 340/635 |
| 5,273,640 | 12/1993 | Kusanagi et al. | 204/401 |

Primary Examiner—John Niebling
Assistant Examiner—Bruce F. Bell
Attorney, Agent, or Firm—Jim Zegeer

[57] ABSTRACT

A system and method of detecting the end of useful life in a gas sensor cell having a cathode, anode, one of which is consumable, and an electrolyte, and a circuit for controlling the flow of gas to the cell and a sensing resistor and circuit connected to said cathode and said anode, the consumable electrode is provided in the form of a plurality of discrete elements which are sequentially connected in circuit with the other electrode, sensing resistor and circuit. A drop in current between respective ones of the consumable electrode is an indication of the approach of the end of the useful life of the gas sensor.

12 Claims, 2 Drawing Sheets

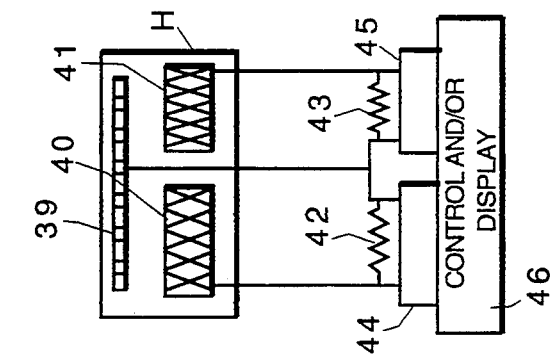
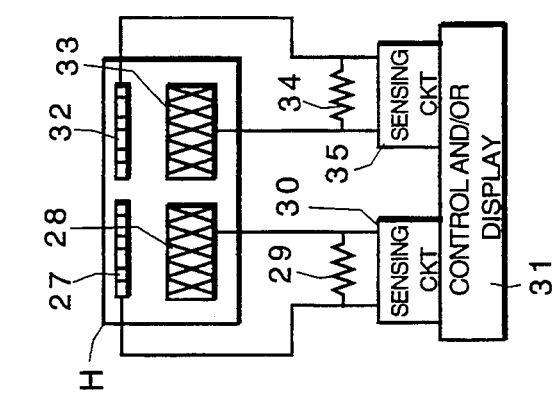
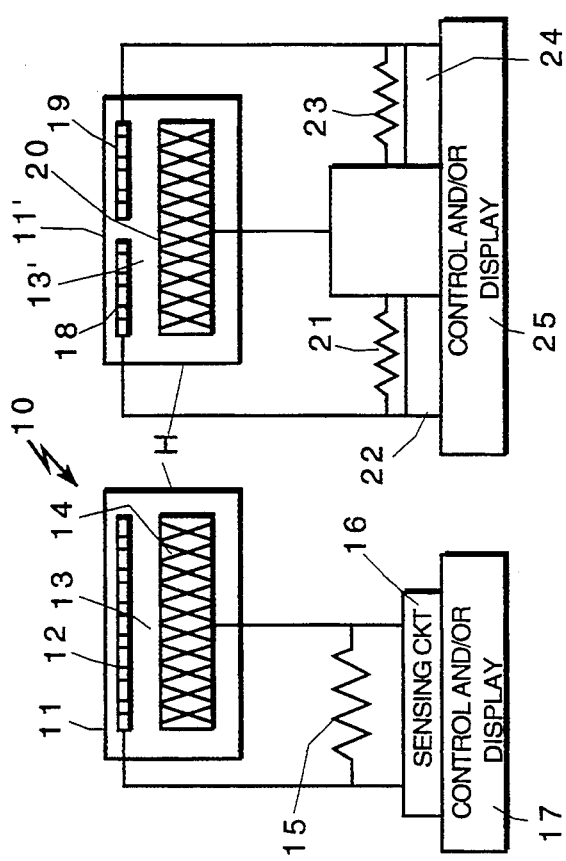
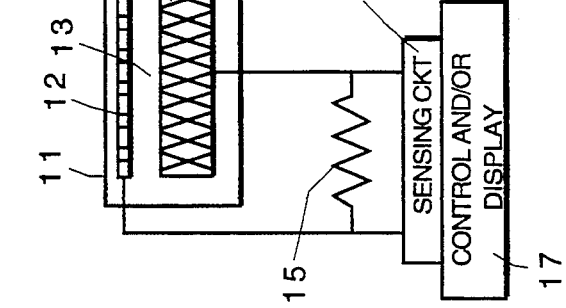

GAS SENSOR AND METHOD

The present invention is directed to electro-chemical sensors of the type which have consumable electrodes and related electronic circuits, and which can operate on either galvanic or polarographic principles.

A commonly used prior art system (FIG. 1a) comprises a housing, a cathode (or sensing electrode), one or more consumable anodes (counter-electrodes), electrolyte, and a gas limiting control member such as a gas permeable membrane or gas diffusion membrane or, in some cases, a capillary structure (any of which flow limiters may be used to limit movement of the gas to be sensed to the sensing electrode.)

When the cathode electrode and the anodes are connected in a sensing circuit, the magnitude of the current flow measured is proportional to the gas being sensed at the cathode (sensing electrode) which may be any of a number of active materials such as gold, silver, platinum, nickel, etc., the selection criteria for which is known to those skilled in the art. Electrochemical reduction takes place at the cathode, and the anode (lead or copper, for example, which supplies the electrons to permit the reduction) is consumed.

When the anode of such a cell is in the last stages of being expended, it may fail between calibrations. This may cause serious problems. For example, if such a cell is used as an oxygen ($O_2$) sensor in a control circuit for a baby isolette, the control valve which adds $O_2$ to the isolette is caused to open and add too much oxygen to the baby isolette thereby possibly blinding or otherwise injuring the baby.

In some prior art units, dual cathode sensing circuits (FIG. 1b) have been provided with the sensor components in a common housing. While these redundancy-type units serve some purpose, they do not tell the user when the end of anode life is approaching any more accurately than a single cell/circuit unit.

It has been suggested (FIG. 1d) that a common cathode/dual anode system with one of the anodes being somewhat smaller than the other anode, and with a detection circuit to measure the current from each anode, could provide a solution to the problem. It is believed that this cannot work as a practical means of detecting remaining anode life since the electrons, at any particular time, may come from either anode in whatever proportion is dictated by uncontrollable phenomena, and this proportion will continually vary with time. In other words, the amount of useable material remaining in the anodes will not determine which anode supplies a preponderance of electrons at any given time during the normal life of the cell. It is understood that the total number of electrons which are being provided by the anode(s) in a properly functioning sensor is determined by the number of gas molecules available to be reduced at the cathode and not by the state of the anode. Otherwise, it would not be a gas sensor.

The object of the present invention is to provide a solution to the problem of end-of-life anode consumption and sudden sensor failure.

The present invention takes a new approach to solving the problem. According to the present invention, a common cathode and sensing circuit are switched or multiplexed back and forth in alternating sequence between two or more anodes. The sensing circuit is in addition to measuring the current flow to determine gas concentration, designed to detect a variation in signal as a function of which anode is being used to supply the electrons in the reaction. The system then knows that a given anode of the cell is reaching the end of its useful life when it can no longer supply electrons at the same rate as the other anode(s). When the cathode is the consumable electrode, a common anode and sensing circuit is switched or multiplexed between two or more cathodes in similar fashion.

DESCRIPTION OF THE DRAWINGS

The above and other objects, advantages and features of the invention will become more apparent when considered with the following specification and accompanying drawings wherein:

FIG. 1a, 1b and 1c are examples of prior art gas sensor systems, and FIG. 1d is a block diagram of a suggested solution.

DETAILED DESCRIPTION OF THE INVENTION

Figure 2B:
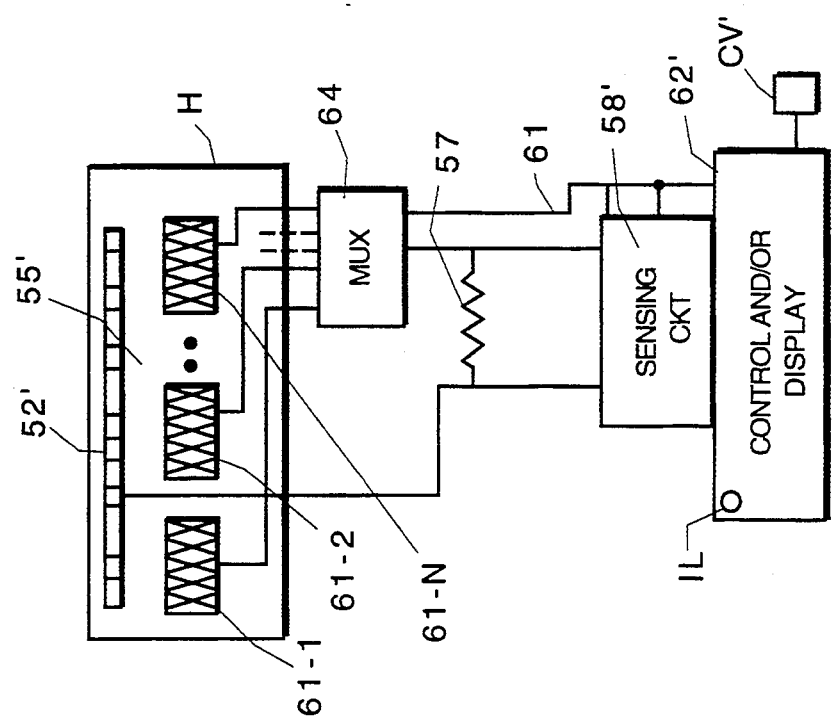
FIG. 2b is a schematic block diagram of a further embodiment of the invention.

Sensors of the type disclosed in FIGS. 1a, and 1b, have been commercially available for a number of years.

FIG. 1a discloses a generic galvanic gas sensor system 10 in which a gas movement or transport control member 11 conveys gas to be sensed to a cathode (sensing electrode) 12, electrolyte 13, and anode 14 which are connected via a load resistor (or resistance network) 15 to sensing circuit 16 which supplies an output signal to a utilization device 17 which may be a control circuit system. The sensor disclosed in FIG. 1a is a galvanic sensor in which there is an electric current in the circuit via resistor 15, between cathode 12 and anode 14. It is adaptable to polarographic operation.

The system of FIG. 1b is similar, except it is a dual unit in which a pair of sensing cathodes 18 and 19 utilize a common anode 20. Cathode 18 and anode 20 are connected in a circuit with a resistor (or resistance network) 21 to provide one output to its related sensing circuit 22, and a second sensing circuit constituted by cathode 19, anode 20, resistor 23, and sensing circuit 24 which supply the second of dual outputs to a control or display circuit 25.

The system shown in FIG. 1c is similar to that shown in FIG. 1b in that it is a dual-type system. A first half is constituted by a cathode electrode 27, anode electrode 28 connected in circuit across a resistor (or resistance network) 29 which, in turn, is connected to a sensing circuit 30 and a control utilization device constituted by control and display unit 31. The second or dual part of the cell is similarly constituted by a cathode electrode 32, anode electrode 33, connected in circuit across a sensing resistor 34 which is coupled to sensing circuit 35 and utilization circuit 31.

The unit shown in FIG. 1d, suggested by others, incorporates a common cathode 39 and a dual anode 40, 41 which are connected, across resistors (or resistance networks) 42 and 43, respectively. One of the anodes is made smaller than the other anodes so that presumably, that anode would be consumed at an earlier time than the larger anode and a drop in the signal from that anode, in comparison to the larger anode would provide a signal, or an indication of, the end-of-life of the sensor.

THE PRESENT INVENTION

Figure 2A:
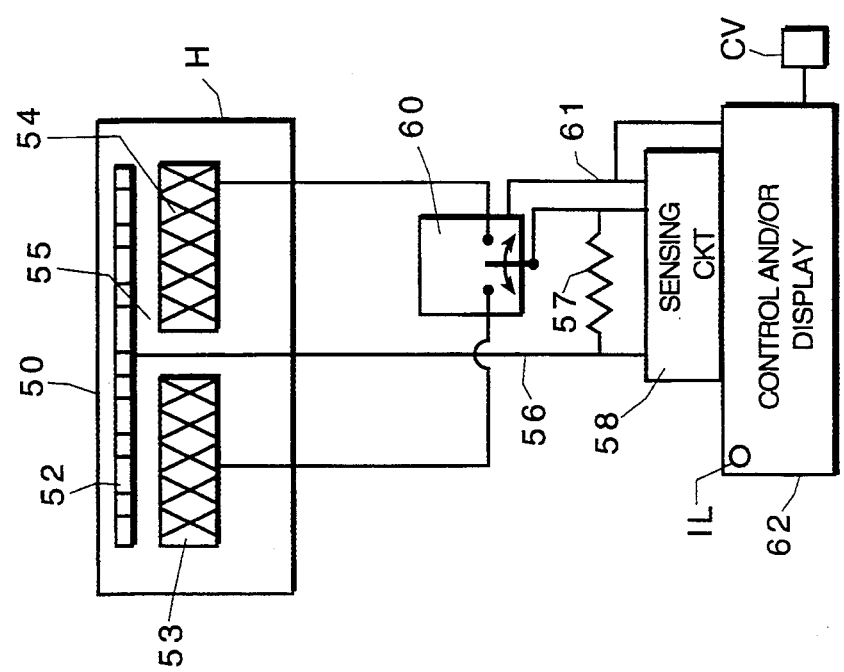
FIG. 2a is a schematic diagram of the sensor system incorporating the invention.

The present invention is depicted in FIGS. 2a and 2b.

In FIG. 2a, an electrochemical gas measuring system is disclosed comprising a gas entry limiting or controlling member 50 which may be a gas diffusion membrane, capillary system or the like, a sensing cathode electrode 52 which may be a conventional gold-plated, perforated disk 52, two or more anode electrodes 53, 54 which are consumable electrodes typically composed of lead or like materials, and an electrolyte 55 (such as potassium hydroxide, for example) housed in a housing H. The cathode electrode 52 is connected by an output lead 56 to one end of sensing or load resistor (or resistance network) 57 and as one input to-the sensing circuit 58. The anode electrodes 53 and 54 are connected to a switch member 60 which may be an electronic switch so that the anode electrodes 53 and 54 are alternately connected in circuit with the cathode electrode 52 so that the current is always flowing through resistor 57 and the position of switch 60 is conveyed to the sensing and control circuit on line 61. Thus, the anode electrode is comprised of at least a pair of electrodes 53, 54 which are sequentially and alternately (in FIG. 2a) connected ill a sensing circuit through sensing resistor 57. The sensing circuit 58 detects a drop in current from any of the anode electrodes relative to the others of the anodes as an indication of the end of the useful life of the sensor. The utilization circuit 62 can operate a control valve CV. In the case of a baby's isolette, in which the mixture of oxygen supplied to the baby must be closely monitored and controlled in order to avoid damage to the baby's eyes, the control valve CV is an oxygen control valve to the baby's isolette. The sensing circuit may include a further circuit for signalling to the user, such as an indicator light IL, that the sensor must be replaced in a short period of time. Meanwhile, the circuit operates on the remaining anode electrode with the user being provided with an indication or warning that the sensor must be replaced in a short period of time.

As noted earlier, the gas entry limiting means can be a gas diffusion membrane, or capillary, or the like. Moreover, the control system or control circuit 62 is preferably programmed or adapted to control the oxygen level based on other than the lower (lowest) of the anode currents e.g., the higher (highest) of the anode currents.

In the embodiment shown in FIG. 2a, a gaseous diffusion membrane 50 constitutes the gas entry limiting means. In FIG. 2b, the gas entry limiting means can be a capillary-type member 52'. In this embodiment, the cathode or sensing electrode 52' is common to a plurality of anodes 61-1, 61-2 . . . 61-N with a scanning switch or multiplexer 64 individually connecting the anode electrodes 61-1, 61-2 . . . 61-N in sequence in circuit with sensing resistor 57' and cathode electrode 52'. High speed scanning switch or multiplexer 64, like switch 60, may dwell on the individual anodes 61-1, 61-2 . . . 61-N for a predetermined interval of time but, the switching time between anodes is extremely rapid so that the sensing circuit is essentially always closed and any gas which enters into the sensor does not build-up to any significant extent so as to adversely affect the current readings.

Inasmuch as the multiplexer can be controlled, and is typically a sequential scanning of the anodes 61-1, 61-2 . . . 61-N, it will be appreciated that the sensing circuit can cause the multiplexer 64 to skip those anode electrodes which have been determined by the sensing circuit to be "consumed" or have reached the end of their respective lives, so that only those anode electrodes which have useful life are actually scanned to the end of the useful life of the last of those to be useful.

It is apparent that the invention is not limited to sensors measuring oxidizing (reducible) gasses (such as $O_2$, $NO_2$, $Cl_2$, etc.) but is also useable with sensors measuring electro-chemically oxidizable gasses such as NO, CO, and $H_2S$. For these gasses the anode is the sensing electrode and the cathode may be expended. For these sensors the same arrangement would be used but with multiple (two or more) cathodes and a single anode. With reference to FIG. 2a, in such a case, the anode would correspond to element 52 and tile cathode would correspond to elements 53 and 54. The basic cell design parameters for such cells are well known to those skilled in the art.

Furthermore, in all of the above, and description of sensors embodying multiple consumable electrodes (with switching between the electrodes) invention, it has been contemplated that a gas entry limiting means is employed. However, sensors which are designed to measure gasses which only constitute a small portion of the gas to which the sensor is exposed (for example $H_2S$ or CO in ambient air) the flow limiting mechanism may not be needed. This is well known to those skilled in the art of gas sensor design. Accordingly, the components 50 and 52, respectively, can be a gas entry means rather than gas entry limiting means.

While the invention in its preferred embodiments have been disclosed and described in detail, it will be appreciated that various other embodiments, modifications and adaptations of the invention will be readily apparent to those skilled in the art.

What is claimed is:

1. In an electrochemical gas measuring system comprising a gas entry means, a sensing cathode electrode, an electrolyte, a consumable anode electrode means and an electrical circuit for sensing current flow between said electrodes as a measure of the gas reaching the sensing electrode, and means indicating the current flowing as a function of gas concentration, the improvement for detecting the approach of the end of the useful life for said anode electrode wherein said anode electrode means is comprised of at least a pair of anodes, switch means for connecting said electrical circuit to said plural anodes and to switch sequentially between said plural anodes, and means for detecting a drop in current having a lowest value from any of said anode electrodes relative to the at least one said pair of said anodes as an indication of the end of the useful life thereof.

2. A gas level control system having a control valve means and means controlled by the measuring system defined in claim 1 for operating said control valve to modify operation of the control system when current sensed from one of said anode electrodes decreases below a set limit from that of at least one of the other anodes.

3. The invention defined in claim 2 or claim 5 wherein the gas controlled is oxygen ($O_2$) and the gas level control system in which said oxygen to be controlled is a life support system.

4. The invention defined in one of claims 2, 6 or 8 wherein the modification to the operation of the control system consists of controlling the oxygen level based on other than the lowest of the anode currents.

5. The measuring system defined in claim 1 wherein the gas to be measured is oxygen ($O_2$) and said consumable anode electrode is lead.

6. The measuring system defined in claim 1 including means connecting said sensing circuit to the remaining ones of said anode electrode and signalling to the user to replace the sensor.

7. The invention defined in claim 1 wherein said gas entry means is a flow limiting gas diffusion membrane.

8. The invention defined in claim 1 wherein said gas entry means is a flow limiting capillary.

9. The invention defined in claim 1 wherein the measuring system utilizes other than the lowest anode current to determine gas level.

10. A method of detecting the end of useful life in a gas sensor cell having a cathode, anode, and an electrolyte, and means for controlling the flow of gas to said cell and a sensing resistor and circuit connected to said cathode and said anode, comprising:
providing said anode in the form of a plurality of discrete anode elements, sequentially connecting said discrete anode elements in circuit with said sensing resistor and circuit, and detecting a drop in current between respective ones of said anodes as an indication of the approach of the end of the useful life of said gas sensor.

11. In an electrochemical gas measuring system comprising a gas entry means, a sensing anode electrode, an electrolyte, a consumable cathode electrode means and an electrical circuit for sensing current flow between said electrodes as a measure of the gas reaching the sensing electrode, and means indicating the current flowing as a function of gas concentration, the improvement for detecting the approach of the end of the useful life for said cathode electrode wherein said cathode electrode means is comprised of at least a pair of cathodes, switch means for connecting said electrical circuit to said plural cathodes and to switch sequentially between said plural cathodes, and means for detecting a drop in current from any of said cathode electrodes relative to at least one of said cathodes as an indication of the end of the useful life thereof.

12. In an electrochemical gas measuring system comprising a gas entry means, a sensing electrode, an electrolyte, a consumable electrode means and an electrical circuit for sensing current flow between said electrodes as a measure of the gas reaching the sensing electrode, and means indicating the current flowing as a function of gas concentration, the improvement for detecting the approach of the end of the useful life for said consumable electrode wherein said consumable electrode means is comprised of at least a pair of consumable electrodes, switch means for connecting said electrical circuit to an alternate one of said at least a pair of consumable electrodes, and means for detecting a drop in current from any of said consumable electrodes as an indication of the end of the useful life thereof.

* * * * *